(12) United States Patent
Mehta et al.

(10) Patent No.: US 12,342,438 B2
(45) Date of Patent: Jun. 24, 2025

(54) SYSTEMS AND METHODS FOR CONTROLLING A MEDICAL LIGHT VIA A SOFTWARE CONFIGURABLE HANDLE ASSEMBLY

(71) Applicant: Stryker Corporation, Kalamazoo, MI (US)

(72) Inventors: Sudhanshu Mehta, Gurdaspur (IN); Robert L. York, Lantana, TX (US); Amber Hildebrand, North Richland Hills, TX (US); Paul Nguyen, Flower Mound, TX (US); William Lowell Jacques, II, Mount Pleasant, SC (US)

(73) Assignee: Stryker Corporation, Portage, MI (US)

( * ) Notice: Subject to any disclaimer, the term of this patent is extended or adjusted under 35 U.S.C. 154(b) by 554 days.

(21) Appl. No.: 17/656,639

(22) Filed: Mar. 25, 2022

(65) Prior Publication Data
US 2022/0312569 A1   Sep. 29, 2022

Related U.S. Application Data

(60) Provisional application No. 63/166,624, filed on Mar. 26, 2021.

(51) Int. Cl.
*A61B 90/30* (2016.01)
*F21V 21/40* (2006.01)
*H05B 47/105* (2020.01)

(52) U.S. Cl.
CPC ........... *H05B 47/105* (2020.01); *A61B 90/30* (2016.02); *F21V 21/403* (2013.01); *A61B 2090/308* (2016.02)

(58) Field of Classification Search
CPC . H05B 47/105; A61B 90/30; A61B 2090/308; F21V 21/403
See application file for complete search history.

(56) References Cited

U.S. PATENT DOCUMENTS

| | | | |
|---|---|---|---|
| 8,643,311 B2 * | 2/2014 | Nevins | H05B 45/20 315/363 |
| 10,653,494 B2 | 5/2020 | Strölin | |
| 2007/0130522 A1 * | 6/2007 | Mansell | G06F 3/0482 715/744 |

(Continued)

FOREIGN PATENT DOCUMENTS

| | | |
|---|---|---|
| WO | 99/50593 A2 | 10/1999 |
| WO | 03/072995 A1 | 9/2003 |
| WO | 2012/151073 A2 | 11/2012 |

OTHER PUBLICATIONS

Office Action dated May 27, 2024, directed to EP Application No. 22 164 377.8; 9 pages.

(Continued)

*Primary Examiner* — Gary Collins
(74) *Attorney, Agent, or Firm* — Morrison & Foerster LLP

(57) ABSTRACT

A method for controlling a medical light by a handle assembly removably mounted to the medical light includes storing configuration data at a controller of the handle assembly that defines a mapping of handle assembly user inputs to medical light property adjustments; detecting a first user input to the handle assembly; and sending a control signal to the medical light to vary a property of light provided by the medical light according to the first user input and the configuration data.

26 Claims, 10 Drawing Sheets

(56) References Cited

U.S. PATENT DOCUMENTS

| | | | |
|---|---|---|---|
| 2008/0259590 A1* | 10/2008 | De Goederen-Oei | G06F 3/04847 362/85 |
| 2009/0128044 A1* | 5/2009 | Nevins | H05B 47/10 315/182 |
| 2009/0227847 A1* | 9/2009 | Tepper | A61B 90/30 600/249 |
| 2014/0111981 A1 | 4/2014 | Watanabe | |
| 2014/0268751 A1 | 9/2014 | Boccoleri et al. | |
| 2015/0332586 A1* | 11/2015 | Hamm | H05B 47/19 340/12.5 |
| 2016/0051132 A1* | 2/2016 | Lia | F21V 23/06 600/249 |
| 2017/0024020 A1* | 1/2017 | Kirkpatrick | G06F 3/0238 |
| 2018/0340679 A1* | 11/2018 | Changeux | F21V 21/403 |
| 2020/0177182 A1 | 6/2020 | Alexanderson et al. | |
| 2021/0239299 A1* | 8/2021 | Westenfelder, II | G02B 3/06 |
| 2022/0151463 A1* | 5/2022 | Fancher | A61B 1/0055 |

OTHER PUBLICATIONS

Extended European Search Report dated Jul. 20, 2022, directed to EP Application No. 22164377.8; 13 pages.

* cited by examiner

SYSTEMS AND METHODS FOR CONTROLLING A MEDICAL LIGHT VIA A SOFTWARE CONFIGURABLE HANDLE ASSEMBLY

CROSS-REFERENCE TO RELATED APPLICATIONS

This application claims the benefit of U.S. Provisional Application No. 63/166,624, filed Mar. 26, 2021, the entire contents of which are hereby incorporated by reference herein.

FIELD

The present invention relates to medical lighting, and in particular, to medical lighting for open field surgery

BACKGROUND

Surgical lights are used in operating rooms to provide relatively high intensity light to a target surgical area for illuminating the target surgical area during open field surgery. The target surgical area may be illuminated by the one or more surgical lights for direct observation by the surgeon. Surgical lights are typically mounted on suspension arms that enable users to adjust the position and orientation of the medical lights. Surgical lights often have a centrally located handle that a user can grasp to reposition the surgical light.

Surgical lights may have multiple user-adjustable attributes that enable a user to customize the light to the user's preferences and the surgical procedure. Examples of user-adjustable attributes include intensity, spot size, and color temperature. Common user interfaces for adjusting such attributes include a control panel on the surgical light housing or the suspension arm, a wall-mounted control panel, and/or the centrally located handle. One advantage of control via the light handle is that the light handle can be provided with a sterile cover such that the surgeon can control the light without breaking sterility. However, the manner in which the light handle may be used to adjust the attributes of the surgical light may not be apparent or intuitive to the surgeon.

SUMMARY

According to various aspects, systems and methods provide configurable control of medical light characteristics by a medical light handle assembly. The medical light handle assembly may be configured to receive different inputs and the medical light characteristics that the different inputs control may be configurable. According to various aspects, the handle assembly may have a controller that sends commands to a controller of the medical light for adjusting one or more characteristics of the light provided by the medical light. In response to a user input to the handle assembly, such as a handle twist or a button press, the handle assembly controller may generate a command based on configuration data that maps handle assembly user inputs to light adjustment commands and may transmit the command to the medical light. Optionally, the configuration data may be received at the handle assembly from the medical light. According to various aspects, upon replacement of a first handle assembly with a second handle assembly, the configuration data may be transmitted to the second handle assembly so that the second handle assembly operates in the same manner as the first handle assembly. According to various aspects, the configuration data that maps handle assembly actuations to light characteristic adjustments can be user-defined, so that a handle assembly control can be tailored to an individual user.

According to an aspect, a method for controlling a medical light by a handle assembly removably mounted to the medical light includes: storing configuration data at a controller of the handle assembly that defines a mapping of handle assembly user inputs to medical light property adjustments; detecting a first user input to the handle assembly; and sending a control signal to the medical light to vary a property of light provided by the medical light according to the first user input and the configuration data.

Optionally, the configuration data is received at the controller of the handle assembly via a communication connection with the medical light. The configuration data may be received from a computing system communicatively connected to the medical light. The mapping of handle assembly user inputs to medical light property adjustments may be modified by a user via the computing system.

Optionally, the configuration data is stored at the medical light and transmitted to the handle assembly.

Optionally, the configuration data is modifiable via one or more user selectors of the handle assembly such that a different mapping can be defined by the one or more user selectors of the handle assembly.

Optionally, the first user input is a first type of input and the property of light is a first property, and the method further comprises: replacing the configuration data stored at the controller with updated configuration data that defines an updated mapping of the handle assembly user inputs to the medical light property adjustments, detecting a second user input that is the first type of input, and sending a control signal to the medical light to vary a second property of light provided by the medical light according to the second user input and the updated configuration data.

Optionally, the first user input to the handle assembly is a first type of user input and the method further comprises detecting a second type of user input to the handle assembly that is different than the first type of user input and sending a second control signal to the medical light to vary a second property of light provided by the medical light according to the second type of user input and the configuration data.

Optionally, the handle assembly user inputs comprise at least one of a twist of a handle and a button press.

Optionally, at least a portion of the configuration data is adjustable via at least one of a user interface at the medical light and a wall control.

Optionally, the method further includes controlling a separate device communicatively connected to the medical light via the handle assembly according to the configuration data. The separate device can be at least one of a plurality of medical lights.

According to an aspect, a handle assembly for removably mounting to a medical light includes a communication link for communicating with the medical light; one or more sensors for sensing one or more user inputs to the handle assembly; and a controller configured to store configuration data that defines a mapping of the one or more user inputs to medical light property adjustments and send control signals to the medical light to vary one or more properties of light provided by the medical light according to the one or more user inputs and the configuration data.

Optionally, the controller is configured to receive the configuration data from the medical light via the communication link.

Optionally, the controller stores default configuration data that can be superseded by configuration data received via the communication link. The handle assembly may include one or more user selectors for defining a default operation of the handle assembly based on the default configuration data.

Optionally, the controller is configured to receive the configuration data from a computing system communicatively connected to the handle assembly.

Optionally, the one or more user inputs comprise at least one of a twist of a handle and a button press.

Optionally, the controller is configured to control a separate device communicatively connected to the handle assembly according to the configuration data.

According to an aspect, a medical light includes a communication link for communicating with a handle assembly removably mounted to the medical light; and a medical light controller configured to: store configuration data that defines a mapping of one or more user inputs to the handle assembly to medical light property adjustments, transmit the configuration data to the handle assembly via the communication link, and control one or more properties of light emitted by the medical light based on control signals received from the handle assembly that are based on the one or more user inputs and the configuration data.

Optionally, the medical light controller is configured to receive updated configuration data from a computing system communicatively connected to the medical light.

Optionally, the medical light includes the handle assembly. The handle assembly may include a handle assembly controller that receives the configuration data from the medical light controller.

According to an aspect, a computing system for configuring a handle assembly to control one or more properties of a medical light to which the handle assembly is removably mounted includes one or more processors, memory, and one or more programs stored in the memory for execution by the one or more processors for: receiving user input for mapping handle assembly user inputs to medical light property adjustments; and transmitting configuration data to a controller of the handle assembly that is removably mounted to the medical light, wherein the configuration data defines the mapping of handle assembly user inputs to medical light property adjustments such that the handle assembly controls one or more properties of the medical light based on the configuration data in response to user inputs to the handle assembly.

Optionally, the computing system stores different mappings associated with different predefined preferences. The different predefined preferences may be associated with at least one of a user profile and a procedure type.

It will be appreciated that any of the variations, aspects, features and options described in view of the systems apply equally to the methods and vice versa. It will also be clear that any one or more of the above variations, aspects, features and options can be combined.

BRIEF DESCRIPTION OF THE DRAWINGS

The invention will now be described, by way of example only, with reference to the accompanying drawings, in which.

DETAILED DESCRIPTION

Figure 1:
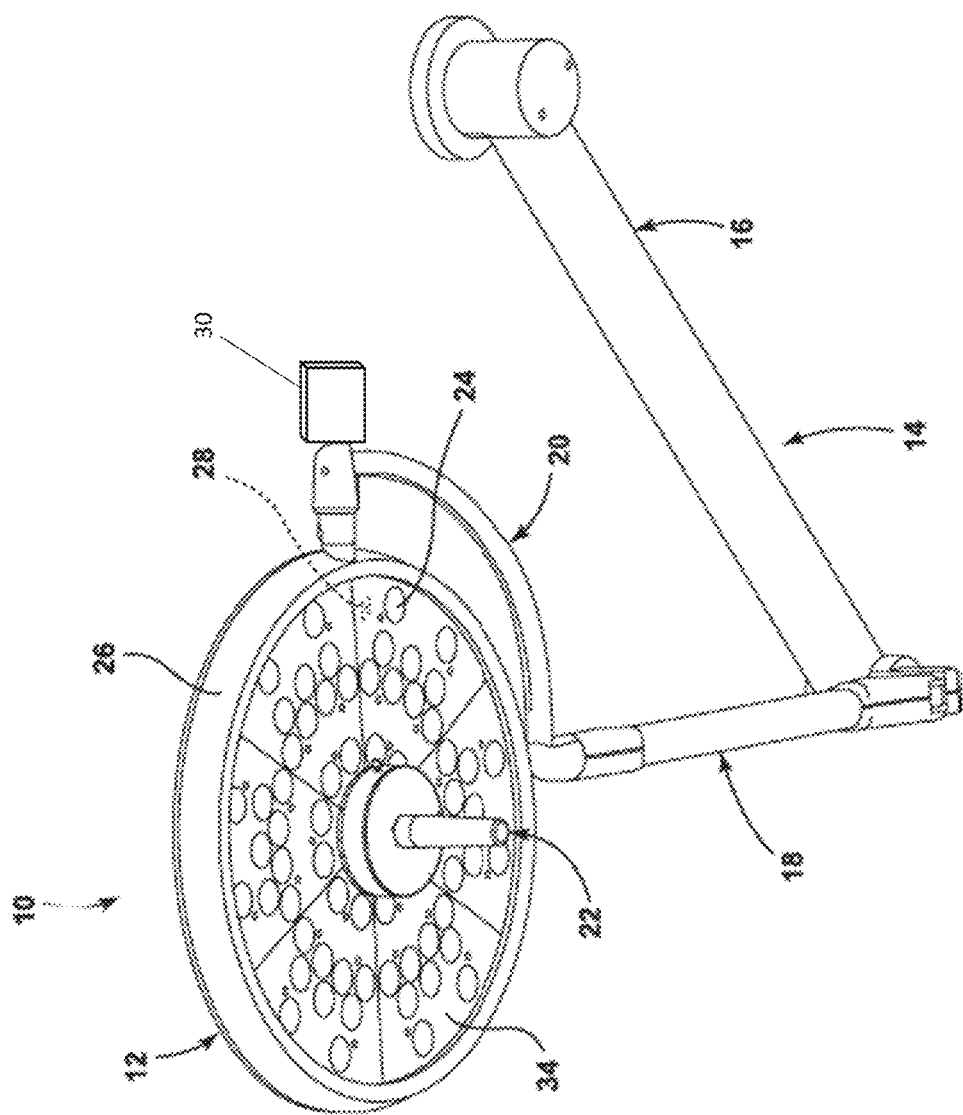
FIG. 1 illustrates an exemplary medical lighting system.

Reference will now be made in detail to implementations and examples of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Systems and methods described here provide control of characteristics of light provided by a medical light via an attached handle assembly in which the manner in which handle assembly user inputs control the light characteristics is software reconfigurable. Configuration data that defines mappings of handle assembly user inputs, such as a handle twists and button presses, to light characteristic adjustments, such as adjusting light intensity, spot size, or color temperature, is stored at the handle assembly and a handle assembly controller responds to a user actuation of the handle assembly by generating a command for adjusting a medical light characteristic based on the configuration data.

The configuration data can be received at a handle assembly from the medical light to which the handle assembly is mounted. Handle assemblies can be swapped out and will operate the same way by receiving the configuration data from the medical light. Therefore, practitioners do not need to reconfigure handles when they switch handles between different medical lights (e.g., in different operating rooms). A handle assembly moved from a first light to a second light that has a different mapping than the first light will behave according to the different mapping by receiving configuration data for the second light.

According to various aspects, the behavior of a handle assembly may be altered by updating the configuration data via a user-interactive controller, such as a medical light-mounted control panel, a wall control, or a computing system communicatively connected to the medical light. A handle assembly may have stored default configuration data that may define behavior of the handle assembly in the absence of configuration data received from the medical light or other device.

In the following description, it is to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure also relates to a device for performing the operations herein. This device may be specially constructed for the required purposes, or it may comprise a general-purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability. Suitable processors include central processing units (CPUs), graphical processing units (GPUs), field programmable gate arrays (FPGAs), and ASICs.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

FIG. 1 illustrates an exemplary medical lighting system 10. The medical lighting system 10 is configured to be positioned within a room (e.g., an operating room) for providing illumination to a desired area of the room. While the medical light system 10 can be placed within an operating room for illuminating a patient for a surgical procedure, the medical light system 10 can also be placed in any area wherein increased light at a targeted location is desired. The medical light system 10 includes a medical light 12 and a suspension arm 14 for connecting the medical light 12 to a static or movable structure within the operating room. For example, the suspension arm 14 can be directly connected to a suspension system connected to a wall or ceiling of the operating room, can be connected to a further arm assembly (not shown) or suspension system directly connected to a wall or ceiling of the operating room, or can be directly or indirectly connected to a movable assembly located within the operating room.

In the illustrated example, the suspension arm 14 of the medical light system 10 allows light from the medical light 12 to be pointed at a certain area within the operating room (with the suspension system allowing the medical light 12 to be selectively positioned within the operating room). The suspension arm 14 includes a first arm member 16 configured to be rotatably connected to a support (e.g., a ceiling), a second arm member 18 rotatably connected to the first arm member 16, and a curved link 20 extending between the second arm member 18 and the medical light 12. The first arm member 16, the second arm member 18 and the curved link 20 allow the medical light 12 to be moved to any desired location by grasping a handle assembly 22 extending from a face of the medical light 12 and pulling, pushing and/or twisting the medical light 12 to any desired location. While a specific suspension arm 14 is illustrated in FIG. 1, any arm well known to those skilled in the art could be used to connect the medical light 12 to the operating room structure or a movable assembly as discussed above (including one connected to multiple points on the side of the medical light 12 and/or the rear surface thereof). The illustrated suspension arm 14 or any arm known to those skilled in the art allows for easy movement of the medical light 12 into any position within the operating room and then maintaining the position of the medical light 12 once released.

The medical light 12 includes a housing 26 having at least one light source 28 (e.g., LED) therein. Each light source 28 is covered by light directing optics 24. The housing 26 includes a circular face glass 34 covering the at least one light source 28, with the handle assembly 22 for moving the housing 26 extending from an opening in the center of the circular face glass 34. Housings for light assemblies and the light sources and optics therein are well known to those skilled in the art. For example, the housing, light source and optics can be those of U.S. Patent Application Publication No. 2014/0268751 entitled MEDICAL LIGHT WITH BEAM REDIRECTING OPTICS, the entire contents of which are incorporated herein by reference. As discussed further below, the handle assembly 22 can also be used to control one or more characteristics of the light provided by the medical light 12 via one or more user inputs to the handle assembly 22, such as one or more buttons presses and clockwise and counterclockwise twists. Characteristics of the light provided by the medical light 12 can also be adjusted via a control panel 30, which can be located on the housing 26 or on the suspension arm 14. The control panel 30 can include one or more buttons, switches, a touch panel, and/or any other user interface suitable for providing user input for altering one or more characteristics of the light provided by the medical light 12.

As noted above, the handle assembly 22 can be actuated to alter characteristics of the medical light 12. Example of actuation methods can include twisting a hand grip portion of the handle assembly 22 (e.g., clockwise and counterclockwise) and pressing one or more buttons of the handle assembly 22. As the handle assembly 22 is actuated (e.g., rotated), characteristics of the medical light 12 can be altered. One characteristic of the medical light 12 that can be altered is an intensity of the light emitted from the at least one light source 28. For example, movement (e.g., rotation)

of the handle assembly 22 can increase or decrease the intensity of the light (i.e., brightness) emitted by the at least one light source 28, turn the light source 28 on, or turn the light source 28 off. More specifically, moving (e.g., rotating) the handle assembly 22 in a first direction can turn the at least one light source 28 on at a first intensity. After releasing the handle assembly 22, the handle assembly 22 will return to an initial position. The handle assembly 22 can then be moved (e.g., rotated) again in the first direction a plurality of times, with each movement (e.g., rotation) increasing the intensity of the at least one light source 28. The handle assembly 22 can be moved (e.g., rotated) in a second direction opposite to the first direction to decrease the intensity of the at least one light source 28, with each successive movement (e.g., rotation) decreasing the intensity of the at least one light source 28 until the at least one light source 28 is at its lowest intensity. The at least one light source 28 may be turned off by turning the handle assembly 22 in the second direction and holding the handle assembly 22 in a furthest moved (e.g., rotational) position for a set period of time.

Another characteristic of the medical light 12 that can be altered is a focus area or spot size of the light emitted from the at least one light source 28. A focus area or spot size could be adjusted by activating or deactivating some, but not all, of the light sources 28 (e.g., activating or deactivating the LEDs that illuminate an outer perimeter of a spot when all LEDs are activated). The focus area or spot size could be altered by moving the at least one light source 28 relative to the optics 24. For altering the focus area or spot size, the handle assembly 22 can be moved (e.g., rotated), with every movement (e.g., rotation) in a first direction cycling through a wider focus area or spot size and every movement (e.g., rotation) in a second direction opposite to the first direction cycling through a smaller focus area or spot size.

Another characteristic of the medical light 12 that can be altered is changing a color of light (e.g., white light color temperature) emitted from the medical light 12. The color of light emitted from the medical light 12 can be changed in any manner well known to those skilled in the art. For example, each of the at least one light sources 28 can include a plurality of LEDs that emit light at different spectra, and movement (e.g., rotation) of the handle assembly 22 can activate and/or alter the intensity of LEDs that emit light at a first spectrum to illuminate the target with light having the first spectrum and further movement (e.g., rotation) of the handle assembly 22 can activate and/or alter the intensity of LEDs that emit light at a second spectrum to illuminate the target with light having the second spectrum. Instead of, or in addition to, activating/deactivating or altering intensity of different color LEDs, a mechanical system can be activated that places different colored filters over the at least one light source 28 during movement (e.g., rotation) of the handle assembly 22. Optionally, movement of the handle assembly can cycle between different light color presets. For example, a series of rotations of the handle assembly 22 can sequentially move through light color presets, such as different white light color temperatures. Optionally, one or more presets may be configured to provide contrast enhancement, such as by providing a lower level of red light (relative to white light) to reduce the amount of reflected red light from the illuminated scene.

Figure 2:
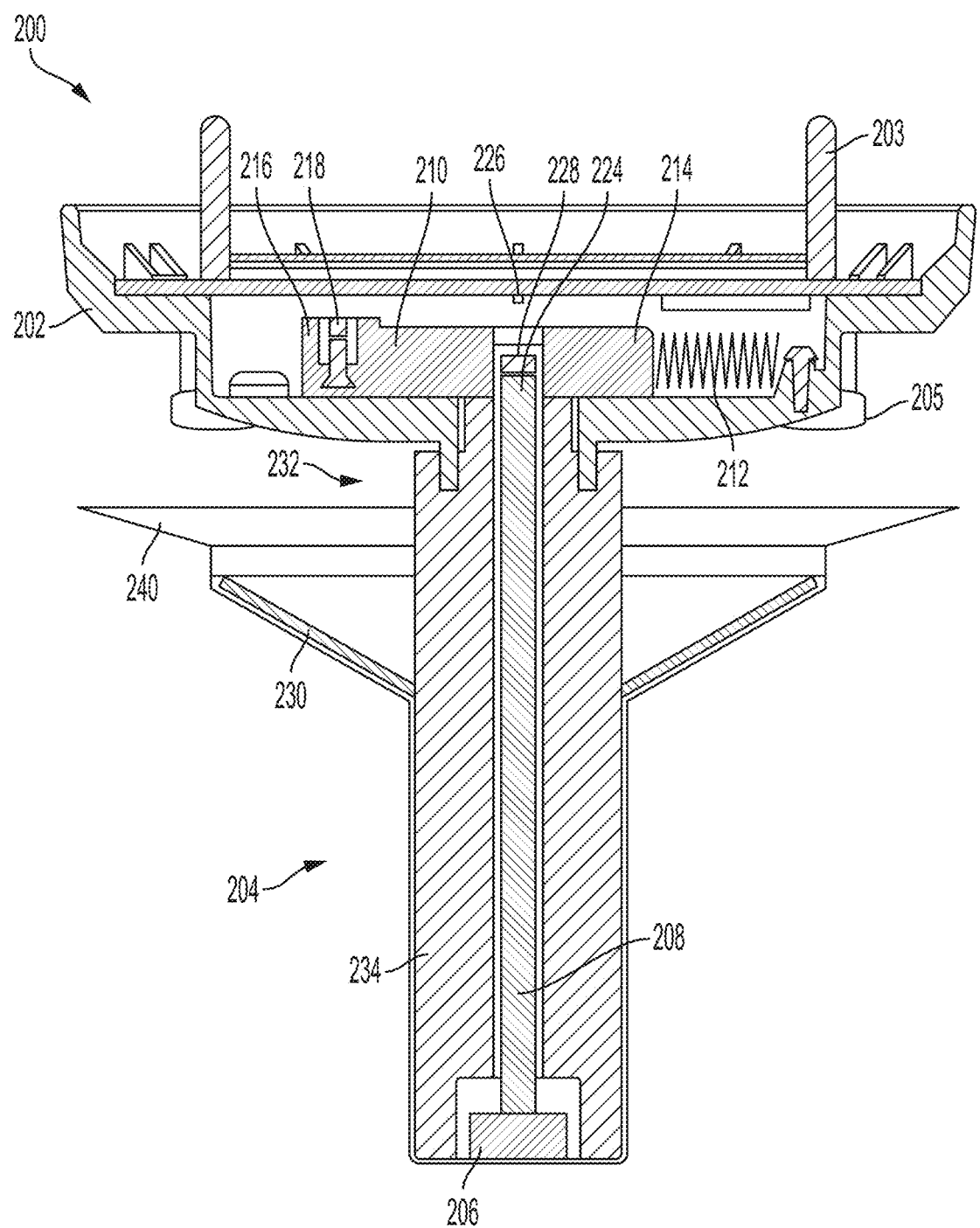
FIG. 2 is a cross-section of an exemplary medical light handle assembly.

FIG. 2 is a cross-section of an exemplary medical light handle assembly 200. Handle assembly 200 can be used to adjust one or more properties of light emitted from a medical light, such as medical light 10 of FIG. 1. Handle assembly 200 includes a base 202 for mounting the handle assembly 200 to the medical light. The base 202 can include a plurality of mounting features 203, such as screws, for mounting the base 202 to the medical light. Handle assembly 200 can be configured for removable mounting to a medical light, such as medical light 10 of FIG. 1. As used herein, "removably" means that the handle assembly 200 is configured such that a user can remove the handle assembly 200 during normal use of the medical light and handle assembly, such as to move the handle assembly to a different medical light. In the example illustrated in FIG. 2, the mounting features 203 for mounting the handle assembly 200 to the medical light are thumb screws with heads 205 that are designed for a user to grasp and turn without the user needing a tool so that the handle assembly 200 can be removed and mounted to a medical light by the user (e.g., a surgeon, a nurse, a medical technician, and/or other medical personnel).

Figure 3:
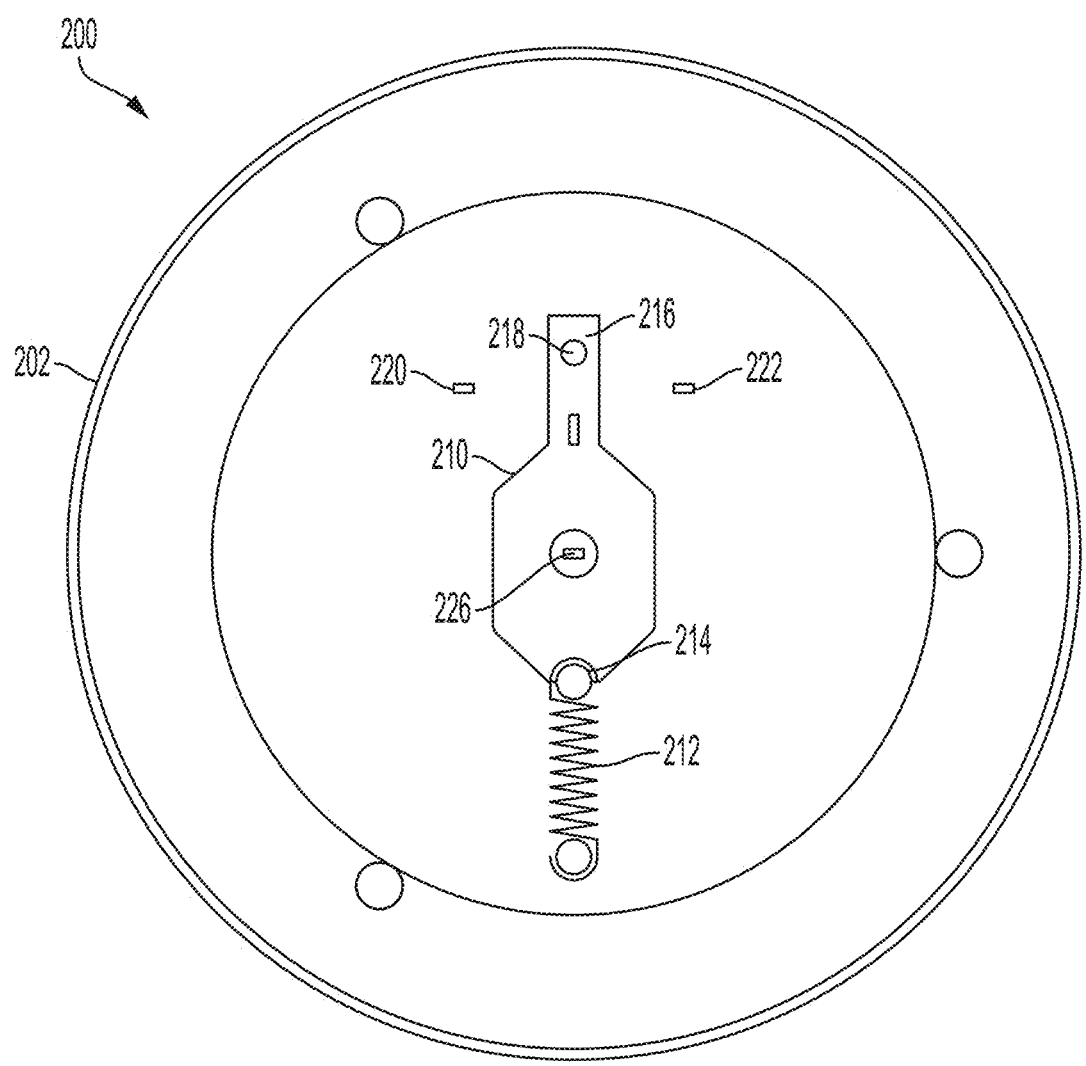
FIG. 3 illustrates a portion of the medical light handle assembly of FIG. 2.

The handle assembly 200 includes a handle 204 that extends from the base 202. The handle 204 may be rotatably mounted to the base 202 such that the handle 204 can be rotated relative to the base 202 to adjust one or more properties of the light of the medical light to which the handle assembly 200 is mounted. The handle 204 may be fixedly connected to an arm 210 located in the base 202. A spring 212 may be connected at one end to a first end 214 of the arm 210 and at the other end to the base 202. The spring 212 biases the arm 210 in a neutral position, which, in turn, biases the handle 204 in a neutral position. The second end 216 of the arm 210 can be used to detect rotation of the handle 204. In the illustrated example, for example, a magnet assembly 218 is mounted at the second end 216 of the arm 210. Upon rotation of the handle 204, the arm 210 rotates and the magnet assembly 218 may align with a sensor 220 (e.g., a magnetic field sensor) mounted to the base 202, which is shown in FIG. 3, and the sensor 220 may provide a signal to a controller of the handle assembly 200 indicating that the handle 204 has been rotated in a first direction. A second sensor 222, which is shown in FIG. 3, can be located in the opposite rotational direction to provide a signal when the handle 204 is rotated in a second direction.

The handle assembly 200 may also include a button 206 located in the bottom of the handle 204 for adjusting one or more properties of the light of the medical light to which the handle assembly 200 is mounted. The button 206 may be connected to a shaft 208 that extends longitudinally within the handle 204. The upper end 224 of the shaft 208 may trigger a sensor 226 located in the base 202 when the button 206 is pressed. The sensor 226 may be, for example, a Hall Effect sensor that may sense a magnet 228 mounted to the upper end 224 of the shaft 208 when the button 206 is pressed.

The handle a may include a flange 230 for shielding the base portion 232 of the handle 204. A sterile cover 240 may be removably positioned on a hand grip portion 234 of the handle 204 and may extend over the flange 230. The sterile cover 240 can be disposable and intended for disposal and replacement with a new cover for each sterile session. Alternatively, the sterile cover 240 can be sterilizable such that it can be sterilized and reused repeatedly. The sterile cover 240 may be made of a flexible material that may fit tightly on the hand grip portion 234 of the handle 204. The sterile cover 240 may cover the button 206 but may be sufficiently flexible that the button 206 can be pressed through the cover 240. Alternatively, the sterile cover 240 may include a button mechanism that interfaces with the button 206.

Figure 4:
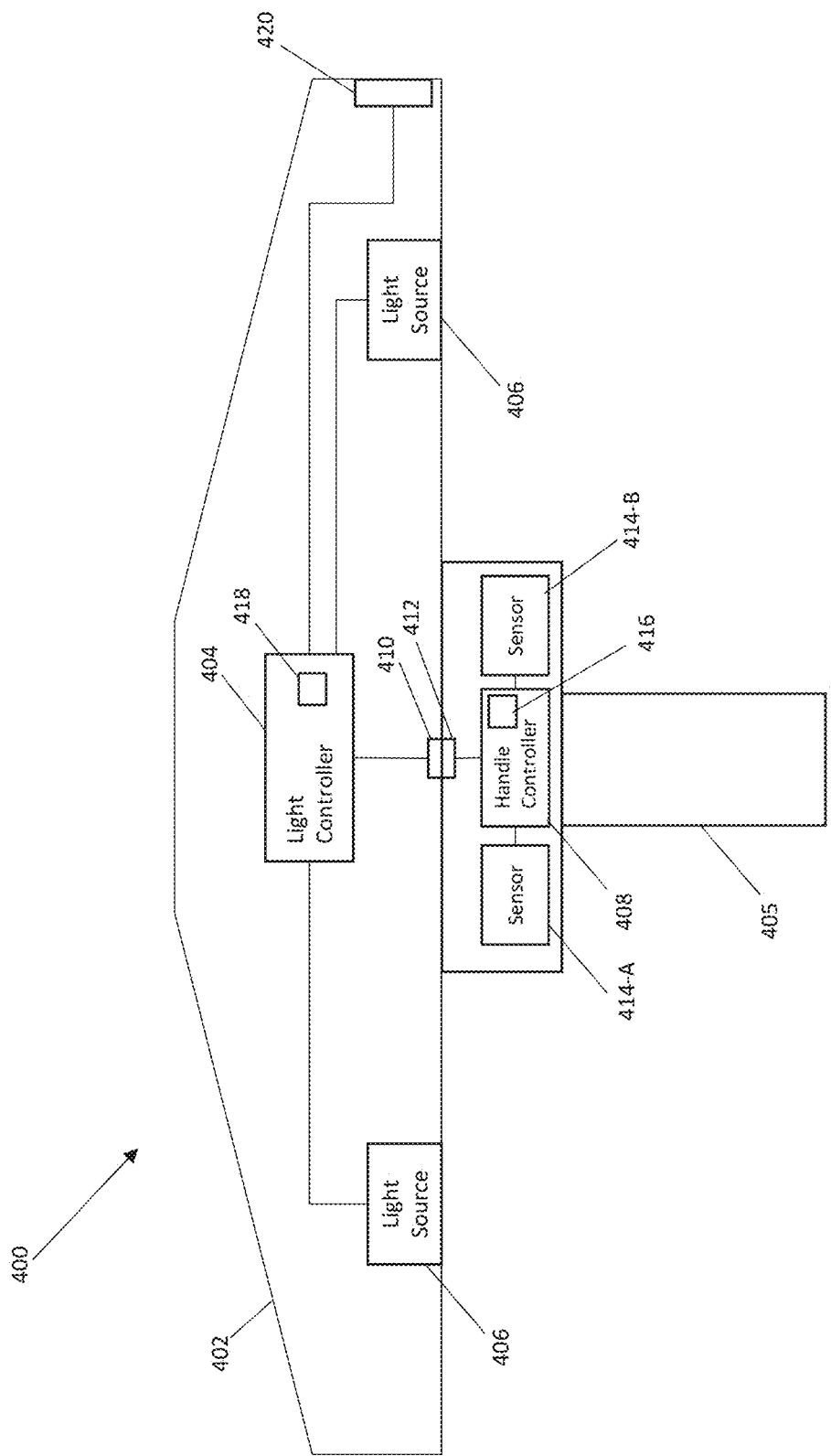
FIG. 4 is a block diagram of an exemplary medical light system that includes a medical light and an attached handle assembly.

FIG. 4 is a block diagram of an exemplary medical light system 400 that includes a medical light 402 (e.g., medical light 12 of FIG. 1) and an attached handle assembly 405 (e.g., handle assembly 22 of FIG. 1). The medical light 402 includes a light controller 404 that is configured to control a plurality of light sources 406 (e.g., light source 28 of FIG. 1) of the medical light 402 according to one or more adjustable characteristics, such as intensity, spot size, color temperature, and turning the light on/off. The light controller 404 can control each light source 406 independently. The light controller 404 can control sets of one or more light sources 406 independently such that a plurality of light sources 406 within a set are controlled together but the set is controlled independently of one or more other sets. A light source 406 includes a plurality of light emitters (e.g., a plurality of LEDs) and the light controller 404 can independently control each light emitter. A plurality of light emitters of a light source 406 may be controlled as a unit. A light source may have its own controller, and the light controller 404 may send commands to the controller of the light source, which may then control the light output of the emitters of the light source.

The handle assembly 405 may include a handle controller 408 that may be communicatively connected to the light controller 404, such as a via respective communication connectors 410 and 412. The handle controller 408 may send one or more light characteristic adjustment commands to the light controller 404 based on one or more user inputs provided to the handle assembly 405. The handle controller 408 may receive signals from one or more sensors 414-A and 414-B that detect user input to the handle assembly 405. For example, sensor 414-A may detect twist of the handle assembly 405 and sensor 414-B may detect a button press. The handle controller 408 may interpret these inputs and may send a corresponding command to the light controller 404 to alter one or more characteristics of the light provided by the medical light 402.

The handle controller 408 may send commands to the light controller 404 that instruct the light controller 404 which light characteristic alteration should be made for a given handle assembly actuation. For example, the handle controller 408 may send an "increase intensity" command to the light controller 404 in response to the sensor 414-A detecting a twist of the hand grip of the handle assembly 405, and the light controller 404 may respond to the "increase intensity" command by increasing the intensity of light provided by the medical light 402. The handle controller 408 may store configuration data, such as in memory 416, that maps handle actuations to specific light adjustment commands to be provided to the light controller 404. For example, the configuration data may map a twist input to a light intensity adjustment command, a button press to a spot size adjustment command, and a twist-and-hold to a color temperature adjustment command. As such, the handle controller 408 does not communicate which user input was received, but rather, communicates the desired adjustment that should be made.

Control of the light characteristics of the medical light 402 by the handle assembly 405 may be reconfigurable by altering the configuration data stored in the memory 416. For example, first configuration data that defines a handle twist as controlling light intensity may be replaced by second configuration data that defines a handle twist as controlling spot size. The configuration data stored in the memory 416 may be updated via the communication link with the medical light 402. Configuration data may be stored in memory 418 of the medical light 402 and transmitted to the handle controller 408. The configuration data stored in memory 418 may be transmitted to the handle controller 408 upon connection of connectors 410 and 412, upon power up of the medical light system 400, and/or at any other suitable time (such as upon a user-defined change in the configuration data). Updated configuration data may be received from an external device, such as an external controller, via a communication connection 420 of the medical light 402.

Figure 5:
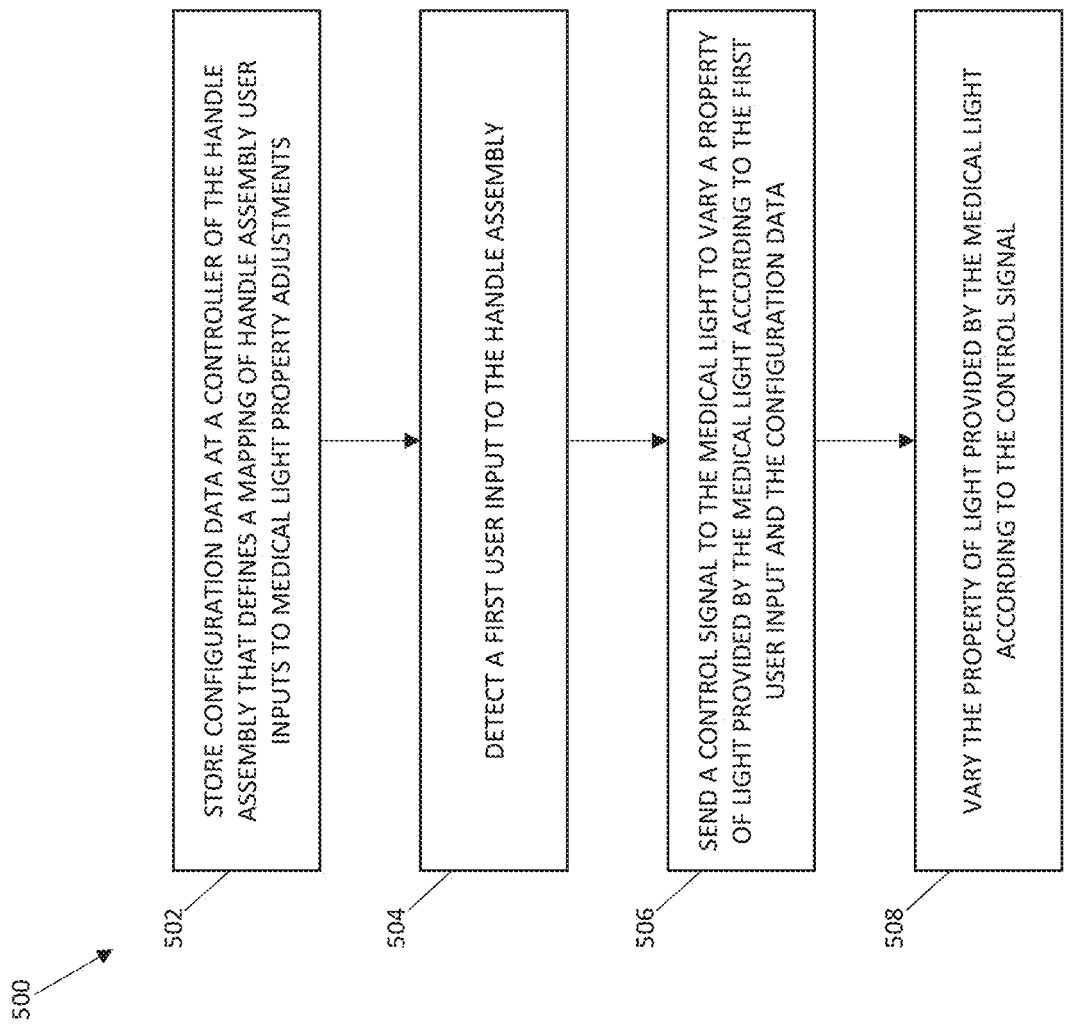
FIG. 5 is a block diagram of an exemplary method for controlling a medical light by a handle assembly mounted to the medical light.

FIG. 5 is a block diagram of an exemplary method 500 for controlling a medical light by a handle assembly mounted to the medical light. Method 500 may be performed, for example, by medical light system 400 of FIG. 4. At step 502, configuration data is stored at a controller of the handle assembly, such as memory 416 of handle controller 408 of FIG. 4, that defines a mapping of handle assembly user inputs to medical light property adjustments. The handle assembly may be configured to receive a plurality of user inputs. Examples of user inputs, include clockwise and/or counterclockwise twisting of a hand grip portion of the handle assembly (e.g., hand grip portion 234 of FIG. 2), a press of button (e.g., button 206 of FIG. 2) of the handle, twist and hold of the hand grip portion, and press and hold of the button. It should be understood that these user inputs are merely exemplary and a handle assembly may include a greater number of user inputs, such as via additional buttons. The configuration data may map each available user input to a light characteristic adjustment. For example, the configuration data may define a twist input as controlling light intensity (e.g., a twist in one direction may increase the intensity and a twist in the opposite direction may decrease the intensity) and a button input as cycling through available spot sizes.

At step 504, a first user input to the handle assembly is detected by the handle assembly. For example, with reference to handle assembly 200 of FIG. 2, a twist of the hand grip portion 234 may be detected by a controller of the handle assembly via a signal from sensor 220 or sensor 222.

At step 506, a control signal is sent by the handle assembly to the medical light to vary a property of light provided by the medical light according to the first user input and the configuration data. For example, the controller (e.g., handle controller 408 of FIG. 4) of the handle assembly may detect a twist of the handle in a first direction and may determine from the configuration data stored at the handle assembly that a twist in the first direction is mapped to increasing the intensity of the light provided by the medical light. The controller may transmit an "increase intensity" command to the controller of the medical light (e.g., light controller 404).

At step 508, the medical light controller controls the light sources of the medical light according to the control signal provided by the handle assembly controller. For example, the medical light controller may control at least a portion of the light sources of the medical light to increase the intensity of light provided by the light sources. The medical light may respond to control signals from the handle assembly in a step-wise fashion. For example, a twist of the handle may result in a fixed increment increase in the intensity of the light provided by the medical light and the intensity may not increase again until the user releases provides a new twist to the handle. Optionally, the handle assembly may be able to control the medical light in a continuous fashion. For example, a twist of the handle may cause the intensity of the light to steadily increase until the handle is released.

Method 500 may include, prior to storing the configuration data at the controller of the handle assembly, receiving the configuration data via a communication connection with the medical light. The configuration data may be stored in a memory of the medical light and transmitted by a controller of the medical light to the handle assembly controller. The configuration data may originate at an external device, such as medical light control panel, a wall control for medical lights in a room, and/or a computing system that is communicatively connected to the medical light, and the configuration data is transmitted to the handle assembly via the medical light. An external device may instruct the medical light controller to transmit configuration data to the handle assembly. An external device may communicate with the handle assembly over a communication bus that extends through the medical light (e.g., CAN bus).

Figure 6:
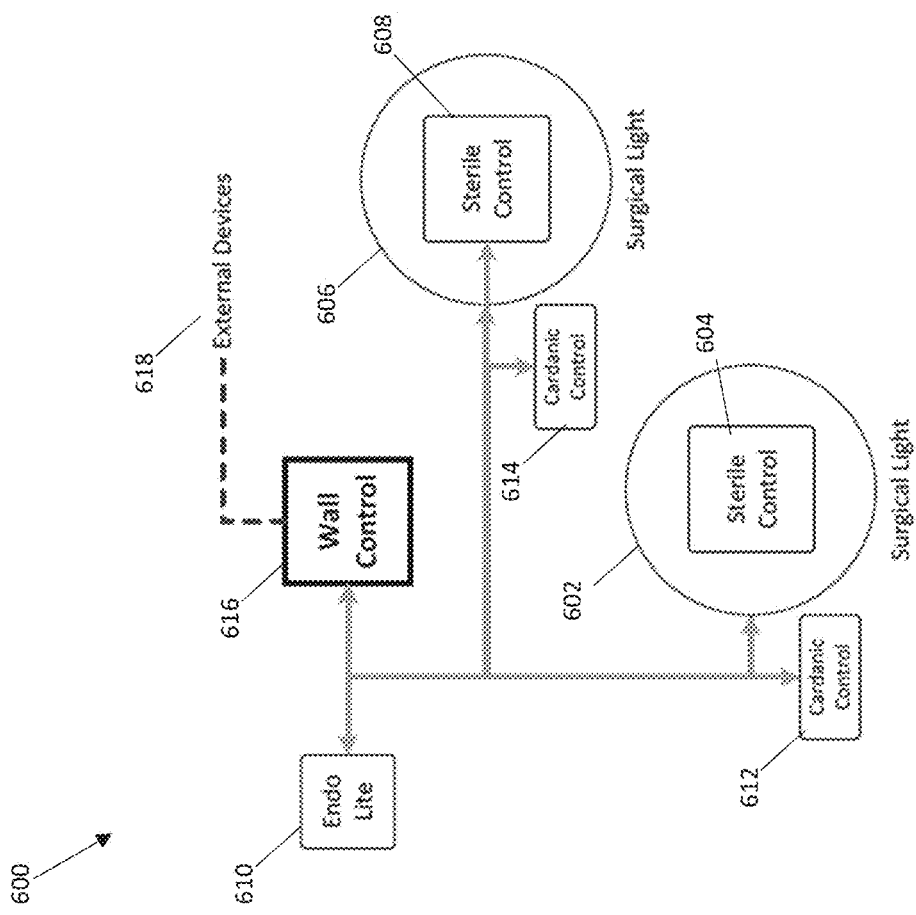
FIG. 6 illustrates an exemplary system for modifying the configuration data stored at the handle assembly.

The handle assembly may be reconfigured (in terms of how particular user inputs control light provided by the medical light) by modifying the configuration data stored at the handle assembly. The configuration data can be modified in a number of ways. FIG. 6 illustrates an exemplary system 600 for modifying the configuration data stored at the handle assembly. System 600 includes a first medical light 602 with an attached first handle assembly 604, a second medical light 606 with attached second handle assembly 608, and a third medical light 610. The first and second medical lights 602, 606 with their respective handle assemblies 604, 608 can be configured, for example, in similar fashion to medical lighting system 10 of FIG. 1 or medical light system 400 of FIG. 4. The third medical light 610 may not have a handle assembly that can be used to control its light output. For example, the third medical light may be a non-task light that can provide ambient light, such as green light, used during minimally invasive procedures when surgical lights are turned off (e.g., after portals are created, trocars inserted, and endoscopic tools are in use). The first, second, and third medical lights 602, 606, 610 may be located in the same location (e.g., the same operating room) or may be located in different rooms (e.g., different operating rooms).

At least one of the first and second medical lights 602, 606 may be provided with a control panel that a user can use to control characteristics of the light provided by the respective medical light. For example, a first control panel 612 may be mounted to the housing of the first medical light 602 or to the suspension system for the first medical light 602 and may be communicatively connected to the controller of the first medical light 602 and a second control panel 614 may be mounted to the housing of the second medical light 606 or to the suspension system for the second medical light 606 and may be communicatively connected to the controller of the second medical light 606. The control panels 612, 614 may include a touch screen, one or more buttons and/or switches, or any other suitable user interface(s) for enabling a user to make adjustments to one or more characteristics of light provided by the medical lights 602, 606. For example, the control panels 612, 614 may include a touch screen with one or more graphical selectors for adjusting properties of the light, such as the intensity, spot size, contrast enhancement, and/or color temperature of the medical light.

System 600 may also include a wall control 616, which may be mounted in the same room as at least one of the medical lights. The wall control 616 may be used to adjust characteristics of the light provided by one or more of the medical lights. The wall control 616 includes a touch screen, one or more buttons and/or switches, or any other suitable user interface(s) for enabling a user to adjust one or more characteristics of light provided by the medical lights 602, 606. Any of the medical lights 602, 606, 610, the handle assemblies 604, 608, the control panels 612, 614, and/or the wall control 616 may be communicatively connected to one another using any suitable communication protocol, including, for example, Controller Area Networks (CAN), Serial Peripheral Interfaces (SPI), Ethernet, RS-485, and Local Interconnect Network (LIN) protocols.

System 600 may include one or more external devices 618 that may be communicatively connected to the system 600, such as via a communication connection to the wall control 616. As used with respect to external device 618, the term "external" means external to the lighting system. The external device 618 may be a computing system located within the same room as one or more of the medical lights. For example, the external device 618 may be a computing system that controls or otherwise interacts with other medical equipment in the same room as at least one of the medical lights, such as one or more imaging devices, one or more recording devices, one or more display devices, etc. An external device can be a general-purpose computing system, such as a personal computer (e.g., via an installed application or a web application) or smartphone (e.g., via an app), that is communicatively connected to the wall control 616 via one or more communication networks, such as a hospital network. An external device can be a cloud service that is in network communication with the wall control 616. An external device can be a non-transitory computer readable medium, such as a memory card, storing configuration data. The storage medium may be connected to the wall control 616 and/or into a computing system communicatively connected to the wall control 616 to provide the configuration data stored on the storage medium.

One or more of the medical lights 602, 606, 610, the handle assemblies 604, 608, the control panels 612, 614, and/or the wall control 616 can be communicatively connected to one another via a first network and one or more external devices 618 are connected to the wall control 616 via a second network that is distinct from the first network. As such, one or more external devices 618 may communicate with one or more of the medical lights via the wall control 616.

The control panels 612, 614, the wall control 616, and/or the external device 618 can be used to configure/reconfigure the control of one or more of the handle assemblies 604, 608 by providing updated configuration data that provides an updated mapping of handle actuations to light characteristic change commands. For example, the control panels 612, 614, the wall control 616, and/or the external device 618 may include a user interface for a user to define handle assembly control.

Figure 7:
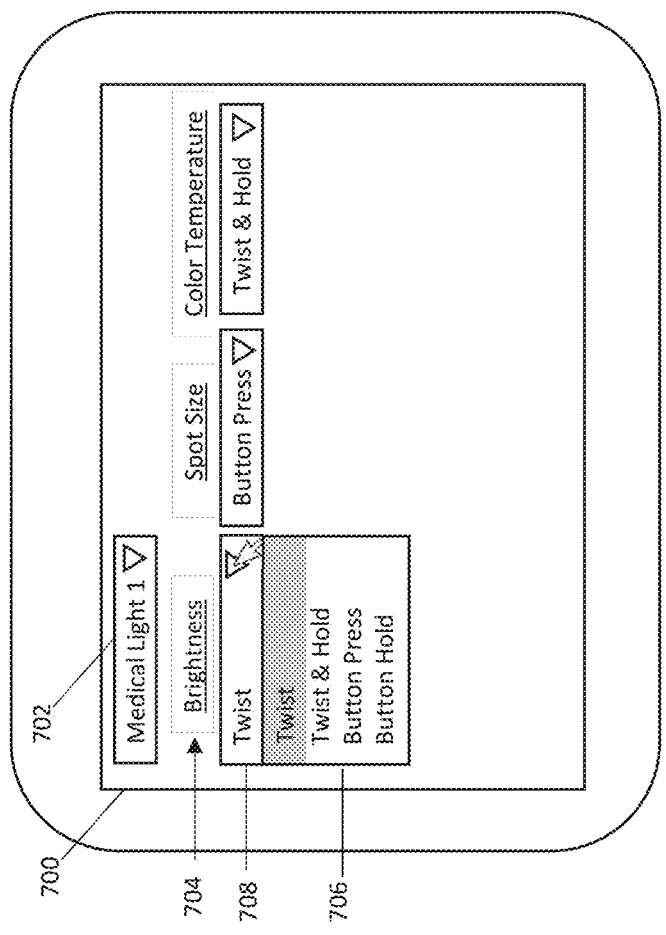
FIG. 7 is an example of a user interface that can be used to modify the configuration data that defines the mapping of handle actuations to light characteristic change commands.

FIG. 7 is an example of a user interface 700 that can be used to modify the configuration data that defines the mapping of handle actuations to light characteristic change commands. User interface 700 can be implemented by any one of the control panels 612, 614, the wall control 616, and/or the external device 618. User interface 700 includes a selector 702 for selecting the medical light for which the handle controls are to be configured. User interface 700 includes the light characteristics 704, the currently selected handle actuation 708 for controlling the respective characteristic, and a drop-down menu 706 for each light characteristic that includes selectable options for handle actuation. Thus, a user can configure the handle assembly connected to the selected "Medical Light 1" by selecting the desired options in the user interface 700. Once the user has made the desired selections, the control device sends updated configuration data to the handle assembly connected to the selected medical light (e.g., Medical Light 1) either directly or via the controller of the selected medical light. Thus, for example, the handle actuation used to control intensity of the Medical Light 1 by an attached handle assembly can be changed from a handle twist to a button press via the user interface 700.

The user interface 700 may be configured for adjusting other aspects of the handle-based control of the medical lights, including, for example, the amount of hold time for a "twist-and-hold" and/or button hold actuation of the handle. A plurality of different hold periods may be defined for providing additional levels of control. For example, a first hold period for a twist may adjust a first characteristic and a second hold period for a twist may adjust a second characteristic.

Different configuration data may be provided for each medical light 602, 606, such as by selecting each light via selector 702 of user interface 700. For example, medical lights 602 and 606 can be configured such that a twist of a handle mounted to medical light 602 can adjust the intensity of the light provided by medical light 602 and a twist of a handle mounted to medical light 606 can adjust a spot size of the medical light 606. The configuration data for a respective medical light may be provided to a handle assembly when it is mounted to the medical light. Thus, for example, handle assembly 604, when mounted to medical light 602, may adjust the intensity of the light provided by medical light 602 and, when dismounted from medical light 602 and then mounted to medical light 606, may adjust the spot size of medical light 606.

The system 600 may be configured such that at least one of the handle assemblies 604, 608 can control other lights than the light that the light to which the handle assembly is mounted. For example, handle assembly 604 can control medical light 602, medical light 606, and/or medical light 610 simultaneously. This can be advantageous where, for example, the medical lights 602, 606, and/or 610 are targeted at the same operating table and the surgeon can adjust all lights illuminating the patient together. This can also be advantageous where a medical light, such as medical light 610, does not have its own light characteristic controlling handle assembly.

Optionally, a user interface, such as user interface 700, can be used to deactivate one or more controls. For example, a configuration can include that a twist and/or button press does not alter any characteristics of the light.

Figure 8:
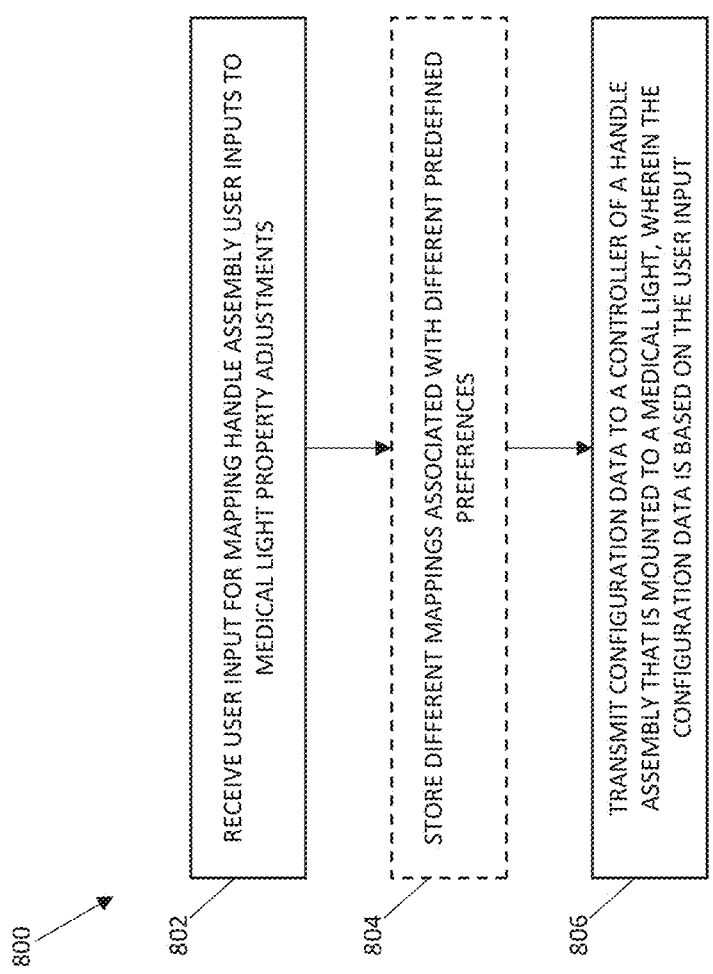
FIG. 8 is a block diagram of an exemplary method for configuring the control of medical light characteristics via a handle assembly mounted to the medical light.

FIG. 8 is a block diagram of an exemplary method 800 for configuring the control of medical light characteristics via a handle assembly mounted to the medical light. Method 800 can be performed, for example, via system 600 of FIG. 6. At step 802, user input is received at a computing device, such as any one of the control panels 612, 614, the wall control 616, and/or the external device 618, for mapping handle assembly user inputs (e.g., twist, twist and hold, one or more buttons presses/holds) to medical light property adjustments (e.g., intensity, spot size, color temperature, etc.). The user input may, for example, include a selection of a specific medical light to which the mapping pertains and selections of mappings of one or more handle assembly user inputs to light property adjustments (e.g., via user interface 700 of FIG. 7).

At step 806, configuration data associated with the user-defined mapping is transmitted to the medical light(s) associated with the user-defined mapping. For example, a user may define or adjust a mapping at wall control 616 of FIG. 6 and the mapping may be transmitted to one or more of the handle assemblies 604, 608. As another example, a user may define a mapping on an app of the user's smartphone (an example of an external device 618 of FIG. 6), the smartphone may upload the mapping to a cloud server (another example of an external device 618 of FIG. 6), the cloud server may communicate with a wall control (e.g., wall control 616 of FIG. 6) located in the room with the medical light, and the wall control may transmit the configuration data defining the mapping to the handle assembly mounted to the medical light (e.g., directly or via the controller of the medical light).

Method 800 may include, at optional step 804, storing different mappings associated with different predefined preferences. The user input received at step 802 can select and/or update one or more of the stored mappings. For example, first and second surgeons may have profiles stored on a hospital server that includes configuration data for first and second predefined mappings, respectively, of handle assembly actuations to medical light characteristic adjustments, and lighting for an operating room can be customized according to the preferences of the first surgeon or the second surgeon by loading the configuration data from the applicable profile onto the handle assemblies for the operating room. This can enable medical lighting in an operating room to be configured for a new user quickly and easily. Alternatively or additionally, one or more predefined mappings may be associated with a medical procedure type and a room can be prepped for a medical procedure by selecting the appropriate medical procedure type, which may automatically reconfigure the medical lights in the room according to the predefined mappings. A wall control (e.g., wall control 616) may store user-defined mappings for easy selection and updating of the handle assemblies and/or may store predefined default mappings that a user may cycle through to select the desired mapping. A user can update predefined preferences (predefined mappings) such as to change the characteristic of at least one medical light that are adjusted for a respective handle assembly user input and/or to change the medical light(s) that are controlled by a respective handle assembly.

A handle assembly may store default configuration data that may define the default operation of the handle assembly in the event that configuration data is not received from another device (e.g., from the medical light and/or from a controller). The default configuration data may be stored, for example, in a memory of the handle assembly, such as memory 416 of handle controller 408 of FIG. 4. The default configuration data may depend on one or more settings that may alterable by a user or servicer. For example, the default configuration data may be updated via any one of the control panels 612, 614, the wall control 616, and/or the external device 618 and, once changed, the default configuration data may be retained until changed again such that upon swapping of the respective handle assembly, the default configuration data may define the handle assembly's behavior on other medical lights when the default configuration is used.

Figure 9:
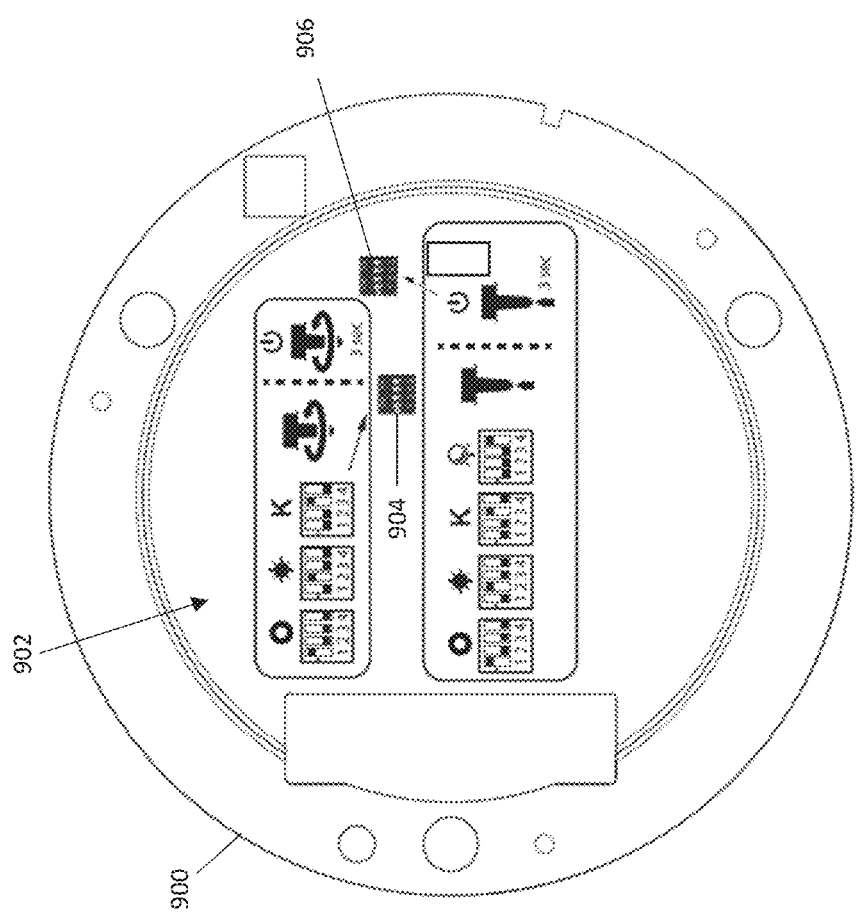
FIG. 9 illustrates an exemplary interface for a user to select a default behavior of a handle assembly.

The default operation of the handle assembly may be alterable via one or more user selectors of the handle assembly. The user selectors may enable a user to select from among a plurality of different default operations as defined by the stored configuration data. FIG. 9 illustrates an exemplary DIP switch interface 902 for a user to select the default behavior of the handle assembly 900. The DIP switch interface 902 may be provided, for example, on a back side of the handle assembly 900 that may be accessible when the handle assembly 900 is unmounted. In the illustrated example, two DIP switch blocks are provided. The first DIP switch block 904 is used to select the handle assembly's behavior upon handle twist, and the second DIP switch block 906 is used to select the handle assembly's behavior upon button press and button hold. In the illustrated example, positioning the first switch of the first DIP switch block 904 in the "on" position with the others in the "off" position selects a twist of the handle actuation to adjusting the spot size, positioning the second switch of the first DIP switch block 904 in the "on" position with the others off maps a twist to adjusting intensity, and positioning the third switch of the first DIP switch block 904 in the "on" position with the others off maps a twist to color temperature adjustment. In the illustrated example, a similar mapping is provided for the button press but with the fourth switch of the second DIP switch block 906 controlling lighting modes. In the illustrated example, both a handle twist and hold and a button hold power the medical light on/off.

Configuration data may be received at a handle assembly controller from the medical light or from a controller communicatively connected to the medical light may take precedence over default configuration data. The default configuration data may be used in the absence of receipt of configuration data, such as where configuration data has not been defined or where a communication link is down.

Figure 10:
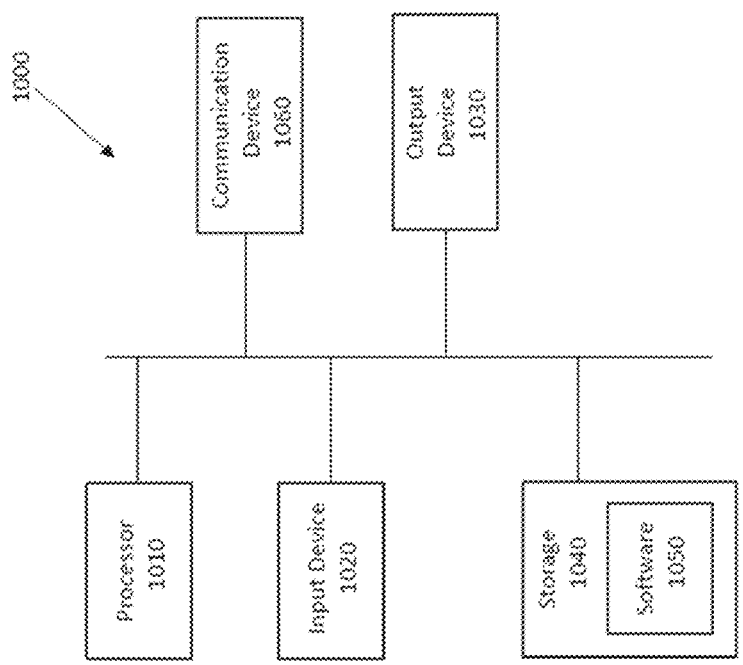
FIG. 10 illustrates an example of a computing system.

FIG. 10 illustrates an example of a computing system 1000 that can be used for one or more of components of system 400 of FIG. 4, such as one or more of light controller 404 and handle controller 408, and/or one or more components of system 600 of FIG. 6, such as controllers of one or more of medical lights 602, 606, 610, controllers of one or more of handle assembly 604 and 608, and one or more of control panels 612, 614, wall control 616, and external device(s) 618. System 1000 can be a computer connected to a network, such as one or more networks of hospital, including a local area network within a room of a medical facility and a network linking different portions of the medical facility. System 1000 can be a client or a server. As shown in FIG. 10, system 1000 can be any suitable type of processor-based system, such as a personal computer, workstation, server, handheld computing device (portable electronic device) such as a phone or tablet, or dedicated device, such as a medical light controller or handle assembly controller. The system 1000 can include, for example, one or more of input device 1020, output device 1030, one or more processors 1010, storage 1040, and communication device 1060. Input device 1020 and output device 1030 can generally correspond to those described above and can either be connectable or integrated with the computer.

Input device 1020 can be any suitable device that provides input, such as a touch screen, keyboard or keypad, mouse, gesture recognition component of a virtual/augmented reality system, or speech-recognition device. Output device 1030 can be or include any suitable device that provides output, such as a display, touch screen, haptics device, virtual/augmented reality display, or speaker.

Storage 1040 can be any suitable device that provides storage, such as an electrical, magnetic, or optical memory including a RAM, cache, SSD, hard drive, removable storage disk, or other non-transitory computer readable medium. Communication device 1060 can include any suitable device capable of transmitting and receiving signals over a network, such as a network interface chip or device. The components of the computing system 1000 can be connected in any suitable manner, such as via a physical bus or wirelessly.

Processor(s) 1010 can be any suitable processor or combination of processors, including any of, or any combination of, a central processing unit (CPU), graphics processing unit (GPU), field programmable gate array (FPGA), and application-specific integrated circuit (ASIC). Software 1050, which can be stored in storage 1040 and executed by one or more processors 1010, can include, for example, the programming that embodies the functionality or portions of the functionality of the present disclosure (e.g., as embodied in the devices as described above). For example, software 1050 can include one or more programs for execution by one or more processor(s) 1010 for performing one or more of the steps of method 500 of FIG. 5 and/or method 800 of FIG. 8.

Software 1050 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1040, that can contain or store programming for use by or in connection with an instruction execution system, apparatus, or device.

Software 1050 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport computer readable medium can include, but is not limited to, an electronic, magnetic, optical, electromagnetic, or infrared wired or wireless propagation medium.

System 1000 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, Ethernet networks, T1 or T3 lines, cable networks, DSL, or telephone lines.

System 1000 can implement any operating system suitable for operating on the network. Software 1050 can be written in any suitable programming language, such as C, C++, Java, or Python. Application software embodying the functionality of the present disclosure can be deployed in different configurations, such as in a client/server arrangement or through a Web browser as a Web-based application or Web service, for example.

The foregoing description, for the purpose of explanation, has been described with reference to specific examples. However, the illustrative discussions above are not intended to be exhaustive or to limit the invention to the precise forms disclosed. Many modifications and variations are possible in view of the above teachings. The examples were chosen and described in order to best explain the principles of the techniques and their practical applications. Those skilled in the art are thereby enabled to best utilize the techniques and various examples with various modifications as are suited to the particular use contemplated. For the purpose of clarity and a concise description, features are described herein as part of the same or separate examples; however, it will be appreciated that the scope of the disclosure includes examples having combinations of all or some of the features described.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A method for controlling a medical light by a handle assembly, the method comprising:
    storing configuration data at a controller of the handle assembly that defines a mapping of handle assembly user inputs to medical light property adjustments;
    detecting a first user input to the handle assembly, wherein the handle assembly is removably mounted to the medical light; and
    sending a control signal to the medical light to vary a property of light provided by the medical light according to the first user input and the configuration data.

2. The method of claim 1, wherein the configuration data is received at the controller of the handle assembly via a communication connection with the medical light.

3. The method of claim 2, wherein the configuration data is received from a computing system communicatively connected to the medical light.

4. The method of claim 3, wherein the mapping of handle assembly user inputs to medical light property adjustments can be modified by a user via the computing system.

5. The method of claim 1, wherein the configuration data is stored at the medical light and transmitted to the handle assembly.

6. The method of claim 1, wherein the configuration data is modifiable via one or more user selectors of the handle assembly such that a different mapping can be defined by the one or more user selectors of the handle assembly.

7. The method of claim 1, wherein the first user input is a first type of input and the property of light is a first property, and the method further comprises:
    replacing the configuration data stored at the controller with updated configuration data that defines an updated mapping of the handle assembly user inputs to the medical light property adjustments,
    detecting a second user input that is the first type of input, and
    sending a control signal to the medical light to vary a second property of light provided by the medical light according to the second user input and the updated configuration data.

8. The method of claim 1, wherein the first user input to the handle assembly is a first type of user input and the method further comprises detecting a second type of user input to the handle assembly that is different than the first type of user input and sending a second control signal to the medical light to vary a second property of light provided by the medical light according to the second type of user input and the configuration data.

9. The method of claim 1, wherein the handle assembly user inputs comprise at least one of a twist of a handle and a button press.

10. The method of claim 1, wherein at least a portion of the configuration data is adjustable via at least one of a user interface at the medical light and a wall control.

11. The method of claim 1, further comprising controlling a separate device communicatively connected to the medical light via the handle assembly according to the configuration data.

12. The method of claim 11, wherein the separate device is at least one of a plurality of medical lights.

13. A handle assembly for a medical light, the handle assembly comprising:
    a communication link for communicating with the medical light;
    one or more sensors for sensing one or more user inputs to the handle assembly; and
    a controller configured to store configuration data that defines a mapping of the one or more user inputs to medical light property adjustments and send control signals to the medical light to vary one or more properties of light provided by the medical light according to the one or more user inputs and the configuration data,
    wherein the handle assembly is configured to be removably mounted to the medical light.

14. The handle assembly of claim 13, wherein the controller is configured to receive the configuration data from the medical light via the communication link.

15. The handle assembly of claim 13, wherein the controller stores default configuration data that can be superseded by configuration data received via the communication link.

16. The handle assembly of claim 15, comprising one or more user selectors for defining a default operation of the handle assembly based on the default configuration data.

17. The handle assembly of claim 13, wherein the controller is configured to receive the configuration data from a computing system communicatively connected to the handle assembly.

18. The handle assembly of claim 13, wherein the one or more user inputs comprise at least one of a twist of a handle and a button press.

19. The handle assembly of claim 13, wherein the controller is configured to control a separate device communicatively connected to the handle assembly according to the configuration data.

20. A medical light comprising:
    a communication link for communicating with a handle assembly removably mounted to the medical light; and
    a medical light controller configured to:
        store configuration data that defines a mapping of one or more user inputs to the handle assembly to medical light property adjustments,
        transmit the configuration data to the handle assembly via the communication link, and
        control one or more properties of light emitted by the medical light based on control signals received from the handle assembly that are based on the one or more user inputs and the configuration data.

21. The medical light of claim 20, wherein the medical light controller is configured to receive updated configuration data from a computing system communicatively connected to the medical light.

22. The medical light of claim 20, wherein the medical light comprises the handle assembly.

23. The medical light of claim 22, wherein the handle assembly comprises a handle assembly controller that receives the configuration data from the medical light controller.

24. A computing system for configuring a handle assembly to control one or more properties of a medical light to which the handle assembly is removably mounted, the computing system comprising one or more processors, memory, and one or more programs stored in the memory for execution by the one or more processors for:
    receiving user input for mapping handle assembly user inputs to medical light property adjustments; and transmitting configuration data to a controller of the handle assembly that is removably mounted to the medical light, wherein the configuration data defines the mapping of handle assembly user inputs to medical light property adjustments such that the handle assembly controls one or more properties of the medical light based on the configuration data in response to user inputs to the handle assembly.

25. The computing system of claim 24, wherein the computing system stores different mappings associated with different predefined preferences.

26. The computing system of claim 25, wherein the different predefined preferences are associated with at least one of a user profile and a procedure type.

* * * * *